United States Patent
Daum

(10) Patent No.: US 6,907,288 B2
(45) Date of Patent: Jun. 14, 2005

(54) CARDIAC RHYTHM MANAGEMENT SYSTEM ADJUSTING RATE RESPONSE FACTOR FOR TREATING HYPOTENSION

(75) Inventor: Douglas R. Daum, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 179 days.

(21) Appl. No.: 09/879,665

(22) Filed: Jun. 12, 2001

(65) Prior Publication Data

US 2002/0147476 A1 Oct. 10, 2002

Related U.S. Application Data

(63) Continuation-in-part of application No. 09/832,365, filed on Apr. 10, 2001.

(51) Int. Cl.$^7$ .............................................. A61N 1/362
(52) U.S. Cl. ........................................................ 607/17
(58) Field of Search ................................ 600/485, 504, 600/509, 506, 513, 526, 547; 607/4–8, 9, 17–20, 23, 28

(56) References Cited

U.S. PATENT DOCUMENTS

| | | | |
|---|---|---|---|
| 3,340,867 A | 9/1967 | Kubicek et al. | |
| 3,871,359 A | 3/1975 | Pacela | |
| 4,003,379 A | 1/1977 | Ellinwood, Jr. | 128/260 |
| RE30,101 E | 9/1979 | Kubicek et al. | |
| 4,271,192 A | 6/1981 | Wurtman et al. | 424/319 |
| 4,437,469 A | 3/1984 | Djordjevich et al. | |
| 4,450,527 A | 5/1984 | Sramek | |
| 4,470,987 A | 9/1984 | Wurtman et al. | 424/259 |
| 4,472,420 A | 9/1984 | Toth | |
| 4,472,431 A | 9/1984 | Toth | |
| 4,576,183 A | 3/1986 | Plicchi et al. | 600/536 |
| 4,651,716 A | 3/1987 | Forester et al. | 128/1 D |

(Continued)

FOREIGN PATENT DOCUMENTS

| | | | | |
|---|---|---|---|---|
| EP | 0 620 420 A1 | * | 1/1994 | G01F/1/56 |
| EP | 1057498 | | 12/2000 | |
| EP | 1078597 | | 2/2001 | |
| EP | 606301 | | 12/2001 | |
| EP | 1247487 | | 10/2002 | |
| EP | 1275342 | | 1/2003 | |
| EP | 771172 | | 4/2003 | |
| WO | WO-8400227 | | 1/1984 | |
| WO | WO-9304627 | | 3/1993 | |
| WO | WO-9601586 | | 1/1996 | |
| WO | WO-9737591 | | 10/1997 | |
| WO | WO-9738628 | | 10/1997 | |
| WO | WO-9851211 | | 11/1998 | |
| WO | WO-0141638 | | 6/2001 | |
| WO | WO-02053026 | | 7/2002 | |
| WO | WO-02053228 | | 7/2002 | |
| WO | WO-03020364 | | 3/2003 | |

OTHER PUBLICATIONS

Ebert, T J., et al., "The use of thoracic impedance for determining thoracic blood volume changes in man", *Aviat Space Environ Med.*, 57(1), (Jan. 1986),49–53.

Primary Examiner—Jeffrey R. Jastrzab
Assistant Examiner—Frances P. Oropeza
(74) Attorney, Agent, or Firm—Schwegman, Lundberg, Woessner & Kluth, P.A.

(57) ABSTRACT

A cardiac rhythm management system detects hypotension, such as by using thoracic impedance to detect a fluid shift away from the thorax. In response to an episode of detected hypotension, it increases a pacing rate response factor mapping a metabolic need to an indicated pacing rate provided by the system. The metabolic need is indicated by an accelerometer, a respiration sensor, or other metabolic need sensor indicating a subject's need for adjusting cardiac output.

34 Claims, 3 Drawing Sheets

U.S. PATENT DOCUMENTS

| | | | |
|---|---|---|---|
| 4,884,576 A | 12/1989 | Alt | 128/419 PG |
| 4,919,136 A | 4/1990 | Alt | |
| 5,031,629 A | 7/1991 | DeMarzo | |
| 5,178,154 A | 1/1993 | Ackmann et al. | |
| 5,246,008 A | 9/1993 | Mueller et al. | 600/508 |
| 5,271,395 A | 12/1993 | Wahlstrand et al. | 607/9 |
| 5,282,840 A * | 2/1994 | Hudrlik | 607/28 |
| 5,284,136 A | 2/1994 | Hauck et al. | 607/24 |
| 5,309,917 A | 5/1994 | Wang et al. | |
| 5,354,317 A * | 10/1994 | Alt | 607/19 |
| 5,441,525 A | 8/1995 | Shelton et al. | 607/23 |
| 5,443,073 A | 8/1995 | Wang et al. | |
| 5,464,434 A | 11/1995 | Alt | 607/6 |
| 5,501,701 A | 3/1996 | Markowitz et al. | 607/9 |
| 5,505,209 A | 4/1996 | Reining | |
| 5,507,785 A | 4/1996 | Deno | 607/24 |
| 5,526,808 A | 6/1996 | Kaminsky | |
| 5,540,728 A | 7/1996 | Shelton et al. | 607/23 |
| 5,562,711 A * | 10/1996 | Yerich et al. | 607/17 |
| 5,626,623 A | 5/1997 | Kieval et al. | 607/23 |
| 5,642,734 A | 7/1997 | Ruben et al. | |
| 5,676,686 A | 10/1997 | Jensen et al. | 607/9 |
| 5,685,316 A | 11/1997 | Schookin et al. | |
| 5,706,829 A | 1/1998 | Kadri | 128/898 |
| 5,725,561 A | 3/1998 | Stroebel et al. | 607/9 |
| 5,725,562 A | 3/1998 | Sheldon | 607/19 |
| 5,749,900 A | 5/1998 | Schroeppel et al. | 607/4 |
| 5,782,774 A | 7/1998 | Shmulewitz | |
| 5,782,884 A | 7/1998 | Stotts et al. | |
| 5,788,643 A | 8/1998 | Feldman | 600/506 |
| 5,791,349 A | 8/1998 | Shmulewitz | |
| 5,800,464 A * | 9/1998 | Kieval | 607/9 |
| 5,865,760 A | 2/1999 | Lidman | |
| 5,874,420 A | 2/1999 | Pelleg | 514/81 |
| 5,876,353 A | 3/1999 | Riff | 600/547 |
| 5,913,879 A * | 6/1999 | Ferek-Petric et al. | 607/14 |
| 5,919,210 A | 7/1999 | Lurie et al. | 607/3 |
| 5,957,861 A * | 9/1999 | Combs et al. | 600/547 |
| 5,957,957 A | 9/1999 | Sheldon | 607/17 |
| 6,026,324 A | 2/2000 | Carlson | 607/27 |
| 6,035,233 A | 3/2000 | Schroeppel et al. | 600/515 |
| 6,044,297 A * | 3/2000 | Sheldon et al. | 607/17 |
| 6,049,735 A | 4/2000 | Hartley et al. | 607/9 |
| 6,076,015 A | 6/2000 | Hartley et al. | 607/20 |
| 6,078,834 A | 6/2000 | Lurie et al. | 607/3 |
| 6,095,987 A | 8/2000 | Shmulewitz et al. | |
| 6,104,949 A * | 8/2000 | Pitts Crick et al. | 600/547 |
| 6,161,038 A | 12/2000 | Schookin et al. | |
| 6,186,955 B1 | 2/2001 | Baura | |
| 6,228,033 B1 | 5/2001 | Koobi et al. | |
| 6,292,689 B1 | 9/2001 | Wallace et al. | |
| 6,317,631 B1 | 11/2001 | Ben-Haim et al. | 607/9 |
| 6,438,408 B1 | 8/2002 | Mulligan et al. | |
| 6,473,640 B1 * | 10/2002 | Erlebacher | 600/547 |
| 6,511,438 B2 | 1/2003 | Bernstein et al. | |
| 6,512,949 B1 | 1/2003 | Combs et al. | 600/547 |
| 6,560,481 B1 | 5/2003 | Heethaar et al. | |
| 6,561,986 B2 | 5/2003 | Baura et al. | |
| 6,602,201 B1 | 8/2003 | Hepp et al. | |
| 6,625,492 B2 | 9/2003 | Florio et al. | 607/17 |
| 6,636,754 B1 | 10/2003 | Baura et al. | |
| 6,748,271 B2 | 6/2004 | Spinelli et al. | |
| 2002/0138014 A1 | 9/2002 | Baura et al. | |
| 2002/0147475 A1 | 10/2002 | Scheiner et al. | 607/17 |
| 2002/0193689 A1 | 12/2002 | Bernstein et al. | |
| 2003/0023279 A1 | 1/2003 | Spinelli et al. | 607/9 |
| 2003/0028221 A1 | 2/2003 | Zhu et al. | 607/9 |
| 2003/0074029 A1 | 4/2003 | Deno et al. | |
| 2003/0191503 A1 | 10/2003 | Zhu et al. | 607/17 |
| 2004/0049235 A1 | 3/2004 | Deno et al. | |

OTHER PUBLICATIONS

Petersen, M E., et al., "Cardiac pacing for vasovagal syncope: a reasonable therapeutic option?", *Pacing Clin Electrophysiol.*, 20(3 Pt 2), (Mar. 1997),824–6.

Spinelli, J. C., "Method and System for Treatment of Neurocardiogenic Syncore", U.S. Appl. No. 10/862,631, filed Jun. 7, 2004, 15 pages.

Sra, J S., et al., "Cardiac pacing during neurocardiogenic (vasovagal) syncope", *J Cardiovasc Electrophysiol.*, 6(9), (Sep. 1995),751–60.

Stahmann, Jeffrey, "Thoracic Impedance Detection with Blood Resistivity Compensation", U.S. Appl. No. 10/921,503, Filed Aug. 19, 2004, 38 pgs.

Mai, J., et al., "Enhanced Rate Response Algorithm for Orthostatic Compensation Pacing", *Pace*, 23, NASPE Abstracts, Abstract No. 678, p. 722, (Apr. 2000).

(Continued)

Luepker, R. V., et al., "Transthoracic Electrical Impedance: Quantitative Evaluation of a Non–Invasive Measure of Thoracic Fluid Volume", *American Heart Journal*, vol. 85, No. 1,(Jan. 1973),83–93.

Berman, I R., et al., "Transthoracic electrical impedance s a guide to intravascular overload", *Arch Surg.*, 102(1), (Jan. 1971),61–4.

Charach, Gideon, et al., "Transthoracic monitoring of the impedance of the right lung in patients with cardiogenic pulmonary edema", *Crit Care Med.*, 29(6), (Jun. 2001), 1137–44.

Ellenbogen, Kenneth A., et al., "Clinical cardiac pacing", *Philadelphia: Saunders*, (1995),219–233.

Kusumoto, F M., et al., "Medical Progress: Cardiac Pacing", *New England Journal of Medicine*, 334(2), (Jan. 11, 1996), 89–98.

Lau, C P., et al., "Rate–responsive pacing with a pacemaker that detects respiratory rate (Biorate): clinical advantages and complications", *Clin Cardiol.*, 11(5), (May 1988),318–24.

Pomerantz, M, et al., "Transthoracic electrical impedance for the early detection of pulmonary edema", *Surgery*, 66(1), (Jul. 1969),260–8.

Shoemaker, W C., et al., "Multicenter trial of a new thoracic electrical bioimpedance device for cardiac output estimation", *Crit Care Med.*, 22(12), (Dec. 1994),1907–12.

Wuerz, Richard C., et al., "Effects of prehospital medications on mortality and length of stay in congestive heart failure", *Annals of Emergency Medicine*, 21(6), (Jun. 1992), 669–74.

Yu, Cheuk–Man, et al., "Early warning of CHF hospitalization by intra–thoracic impedance measurement in CHF patients with pacemakers", *Pacing and Clinical Electrophysiology*, 24, (Apr. 2001),19.

* cited by examiner

CARDIAC RHYTHM MANAGEMENT SYSTEM ADJUSTING RATE RESPONSE FACTOR FOR TREATING HYPOTENSION

CROSS REFERENCE TO RELATED APPLICATION

This patent application is a continuation-in-part of Scheiner et al. U.S. patent application Ser. No. 09/832,365, filed on Apr. 10, 2001, entitled "CARDIAC RHYTHM MANAGEMENT SYSTEM FOR HYPOTENSION," and assigned to Cardiac Pacemakers, Inc., the specification of which is incorporated herein by reference in its entirety.

TECHNICAL FIELD

The present system relates generally to cardiac rhythm management systems and particularly, but not by way of limitation, to such a system for treating hypotension.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers coordinate atrial and ventricular contractions to improve pumping efficiency. Cardiac rhythm management systems also include coordination devices for coordinating the contractions of both the right and left sides of the heart for improved pumping efficiency.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by some patients is hypotension, that is, low blood pressure. Hypotension can result in dizziness, sometimes referred to as presyncope. Hypotension can even lead to unconsciousness, sometimes referred to as syncope. One cause of hypotension is an excess shifting of blood in the circulatory system toward the extremities (arms and legs) and away from vital organs in the patient's head and thorax. This can occur, for example, when the patient changes posture from lying horizontal or sitting with legs elevated to a position in which the patient is sitting or standing erect. Hypotension resulting from such changes in posture is referred to herein as orthostatic hypotension. However, hypotension may also have causes other than changes in posture. For example, maintaining the same posture for an extended period of time (e.g., sitting erect during an intercontinental airplane flight) may also cause hypotension. Moreover, certain cardiovascular disorders may result in hypotension independent of postural changes, or may exacerbate orthostatic hypotension.

For example, disautonomic syncope is a problem with the autonomic nervous system. In normal patients, the autonomic nervous system constricts the blood vessels in the extremities in response to a change to a more upright posture. This venoconstriction of the blood vessels in the extremities reduces the amount of blood that would otherwise shift to the extremities when the patient changes to a more upright posture. In some patients, however, this response by the autonomic nervous system is absent, or is even reversed by a venodilation of blood vessels in the extremities. Such patients are likely to experience hypotension. Moreover, this deficient response by the autonomic nervous system may occur even without changes in posture, leading to hypotension that is not necessarily orthostatic in nature.

Another example of a cardiovascular cause of hypotension is vasovagal syncope. In normal patients, a change to a more upright posture results in an increased heart rate. For example, for a patient that is at rest, the heart rate may temporarily increase from 60 beats per minute (bpm) to 80 bpm when the patient stands up after laying horizontally. In some patients, however, this autonomic response is absent-resulting in a drop in heart rate. This may also lead to hypotension as blood shifts away from the head and thorax into the extremities. Regardless of the cause of hypotension, the resulting symptoms of dizziness or loss of consciousness may be extremely dangerous. This is particularly so for elderly patients who are at increased risk of injury from a fall resulting from the dizziness or loss of consciousness. Hypotension is also an obvious danger for persons operating motor vehicles or other machinery. For these and other reasons, there is a need to treat hypotension to avoid these symptoms and associated risks.

SUMMARY

A cardiac rhythm management system detects hypotension. In response to an episode of detected hypotension, it increases a rate response factor mapping a sensor-indicated metabolic need to an indicated pacing rate.

In one example, the system includes a hypotension condition detection circuit to detect a hypotension condition in a subject and to provide a hypotension detection indicator. A first sensor provides a first sensor signal correlative to the subject's metabolic need for a cardiac output. A pacing therapy output circuit provides therapy to the subject at an indicated rate. A controller is coupled to provide the indicated rate to the pacing therapy output circuit. The controller is also coupled to the hypotension condition detection circuit to receive the hypotension detection indicator. The controller is also coupled to the first sensor to receive the first sensor signal. The controller determines the indicated rate based at least in part on the first sensor signal. The controller includes a rate response factor to relate a component of the first sensor signal to the indicated rate. The rate response factor is adjusted by the controller in response to the hypotension condition indicator.

The system also includes a method. The method includes detecting, in a subject, a condition correlative to hypotension. In response to the detected condition, a rate response factor is adjusted. The rate response factor relates: (a) a pacing rate at which stimulations are delivered to the subject's heart; to (b) a sensor signal that is correlative to the subject's metabolic need for cardiac output.

Other aspects of the invention will be apparent on reading the following detailed description of the invention and viewing the drawings that form a part thereof.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
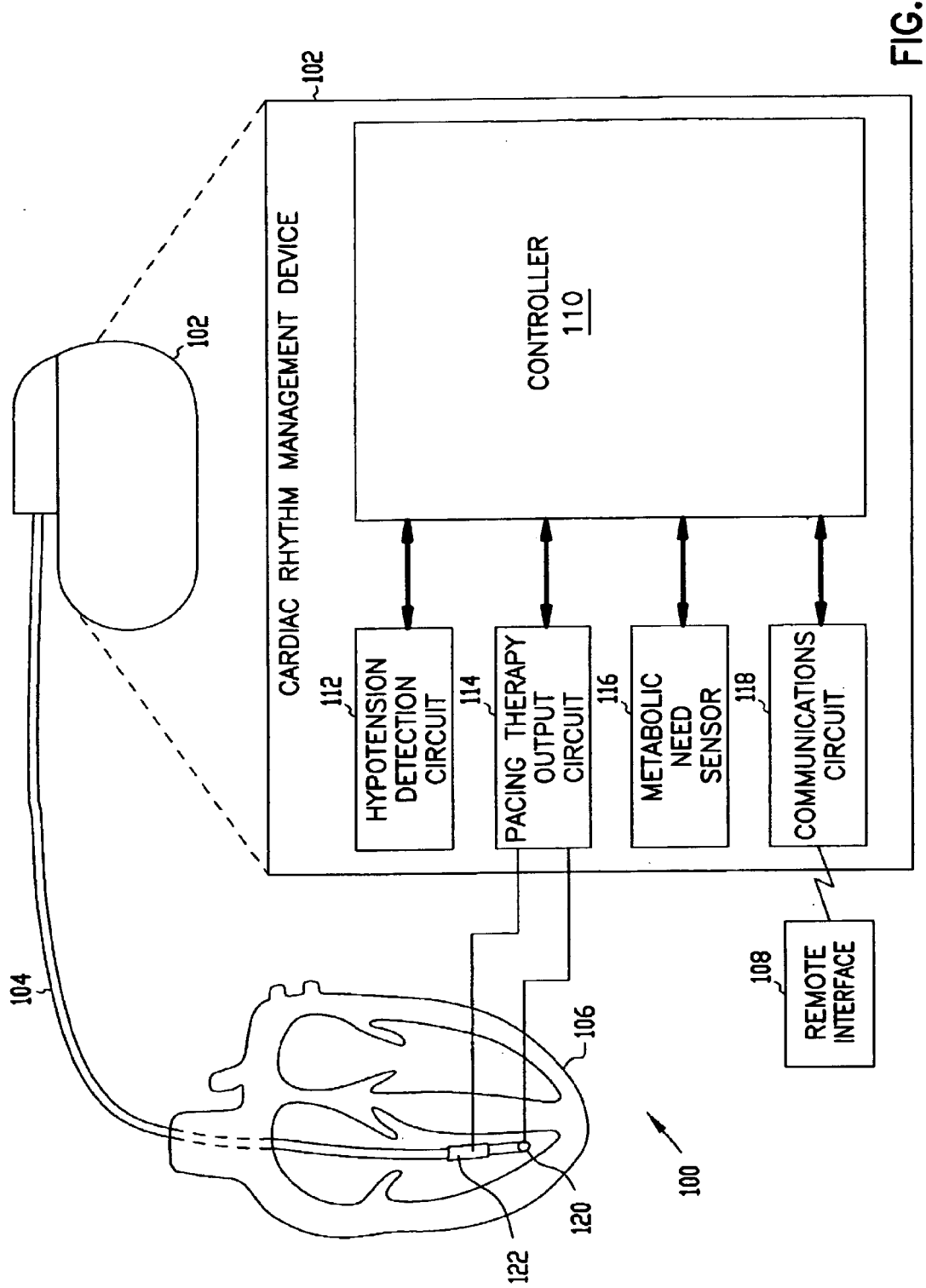
FIG. 1 is a schematic/block diagram example of portions of a cardiac rhythm management system and portions of an environment in which it is used.

FIG. 1 is a schematic/block diagram example of portions of a cardiac rhythm management system 100 and portions of an environment in which it is used. In this example, system 100 includes, among other things, a cardiac rhythm management device 102 and leadwire ("lead") 104, which is coupled to device 102 for communicating one or more signals between device 102 and a portion of a living organism or other subject, such as heart 106. Examples of device 102 include, among other things, bradycardia and antitachycardia pacemakers, cardioverters, defibrillators, combination pacemaker/defibrillators, drug delivery devices, and any other implantable or external cardiac rhythm management apparatus capable of providing therapy to heart 106. System 100 may also include additional components such as, for example, an external or other remote interface 108 capable of communicating with device 102.

In this example, device 102 includes, among other things, a microprocessor or other controller 110 coupled to a hypotension detection circuit 112, a pacing therapy output circuit 114, a metabolic need sensor 116, and a communication circuit 118. Communication circuit 118 is adapted for wireless communication with remote interface 108. Pacing therapy output circuit 114 is coupled to one or more electrodes associated with any chamber(s) of heart 106, such as electrodes 120 and 122 of lead 104, for delivering electrical pacing stimulations for evoking responsive heart contractions. Metabolic need sensor 116 senses the subject's need for a particular degree of cardiac output of blood being pumped through the subject's circulatory system. To accommodate the sensed metabolic need, controller 110 provides pacing therapy output circuit 114 with a variable indicated pacing rate for evoking the heart contractions. A higher sensed metabolic need for cardiac output results in a higher indicated pacing rate for evoking heart contractions.

In this example, hypotension detection circuit 112 detects a hypotension condition in the subject. In response to the detected hypotension, controller 110 adjusts the indicated pacing rate. More particularly, in the presence of hypotension, controller 110 increases a rate response factor ("RRF") so that a particular degree of metabolic need results in an at least temporarily higher indicated pacing rate than if hypotension were not detected. In a further example, controller 110 communicates an indication of the hypotension condition through communication circuit 118 to remote interface 108 for display or other user output.

One example of metabolic need sensor 116 is an activity sensor that senses the subject's activity. A greater activity level corresponds to a greater metabolic need for cardiac output of blood pumped through the circulatory system. One particular example of an activity sensor is an accelerometer for sensing the subject's movement, which is deemed correlative to the subject's activity and, therefore, to the subject's metabolic need. One suitable example of an accelerometer-based activity sensor of metabolic need is discussed in Meyerson et al. U.S. Pat. No. 5,179,947 entitled "ACCELERATION-SENSITIVE CARDIAC PACEMAKER AND METHOD OF OPERATION," which is assigned to Cardiac Pacemakers, Inc., and the disclosure of which is incorporated herein by reference in its entirety. Another example of an activity sensor is a breathing (or "respiration" or "ventilation") sensor that senses the subject's breathing rate. A higher breathing rate is deemed to correspond to a higher activity level, which, in turn, corresponds to a greater metabolic need.

One particular example of a respiration sensor is a transthoracic impedance sensor that detects an impedance across a portion of a subject's thorax ("thoracic impedance" or "transthoracic impedance.") In this document, the term "thorax" refers to the subject's body other than the subject's head, arms, and legs. As the subject breathes, inhaling and exhaling (also referred to as inspiration and expiration) the thoracic impedance varies as modulated by the breathing. From these thoracic impedance variations, the breathing rate can be determined.

In such an thoracic impedance respiration sensor example, metabolic need sensor 116 is coupled to the patient's thorax by at least two electrodes for determining the thoracic impedance by providing a test signal and measuring a response signal. In one suitable thoracic impedance respiration sensor example, system 100 includes a configuration of at least four electrodes for detecting thoracic impedance, such as discussed in Hauck et al. U.S. Pat. No. 5,284,136 entitled "DUAL INDIFFERENT ELECTRODE PACEMAKER," assigned to Cardiac Pacemakers, Inc., the disclosure of which is incorporated herein by reference in its entirety. However, a different number of electrodes (e.g., 2 or 3 electrodes, or more than 4 electrodes) could also be used. One suitable example of a metabolic need sensor 116 based on thoracic impedance detection of respiration uses a high frequency carrier signal to provide a test stimulus and obtain a thoracic impedance response, as discussed in Hartley et al. U.S. Pat. No. 6,076,015 ("the Hartley et al. patent") entitled "RATE ADAPTIVE CARDIAC RHYTHM MANAGEMENT DEVICE USING TRANSTHORACIC IMPEDANCE," assigned to Cardiac Pacemakers, Inc., the disclosure of which is incorporated herein by reference in its entirety.

In this example, hypotension detection circuit 112 detects a hypotension condition in the subject. One example of a suitable hypotension detection circuit 112 is discussed in Scheiner et al., U.S. patent application Ser. No. 09/832,365, filed on Apr. 10, 2001, entitled "CARDIAC RHYTHM MANAGEMENT SYSTEM FOR HYPOTENSION," and assigned to Cardiac Pacemakers, Inc., the disclosure of which is incorporated herein by reference in its entirety. The Scheiner et al. patent application discusses sensing thoracic impedance, such as in the Hartley et al. patent, using an electrode configuration such as that discussed in the Hauck et al. patent.

The thoracic impedance signal is influenced by the patient's thoracic intravascular fluid tension, heart beat, and breathing (also referred to as "respiration" or "ventilation"). A "dc" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz) provides information about the subject patient's thoracic fluid tension, and is therefore influenced by intravascular fluid shifts to and away from the thorax. Higher frequency components of the thoracic impedance signal are influenced by the patient's breathing (e.g., approximately between 0.05 Hz and 2.0 Hz inclusive) and heartbeat (e.g., approximately between 0.5 Hz and 10 Hz inclusive).

As discussed above, a too-low intravascular fluid tension in the thorax ("thoracic hypotension") may result from changes in posture. This is sometimes referred to as orthostatic hypotension. For example, in a person who has been in a recumbent position for some time, approximately ⅓ of the blood volume is in the thorax. When that person then sits upright, approximately ⅓ of the blood that was in the thorax migrates to the lower body. This increases thoracic impedance. Approximately 90% of this fluid shift takes place within 2 to 3 minutes after the person sits upright.

Aside from such changes in posture, however, thoracic hypotension may also manifest itself as disautonomic syncope or vasovagal syncope, or other condition in which intravascular fluid shift from the thorax may or may not correspond directly to a change in the patient's posture. However, hypotension resulting from a fluid shift away from the thorax is indicated by an increase in the baseline thoracic impedance, regardless of whether the cause of the hypotension is orthostatic. In response to the detection of hypotension, controller 110 increases the rate response factor relating the degree of metabolic need sensed by metabolic need sensor 116 to the indicated pacing rate at which pacing stimulations are provided by pacing output therapy circuit 114.

Figure 2:
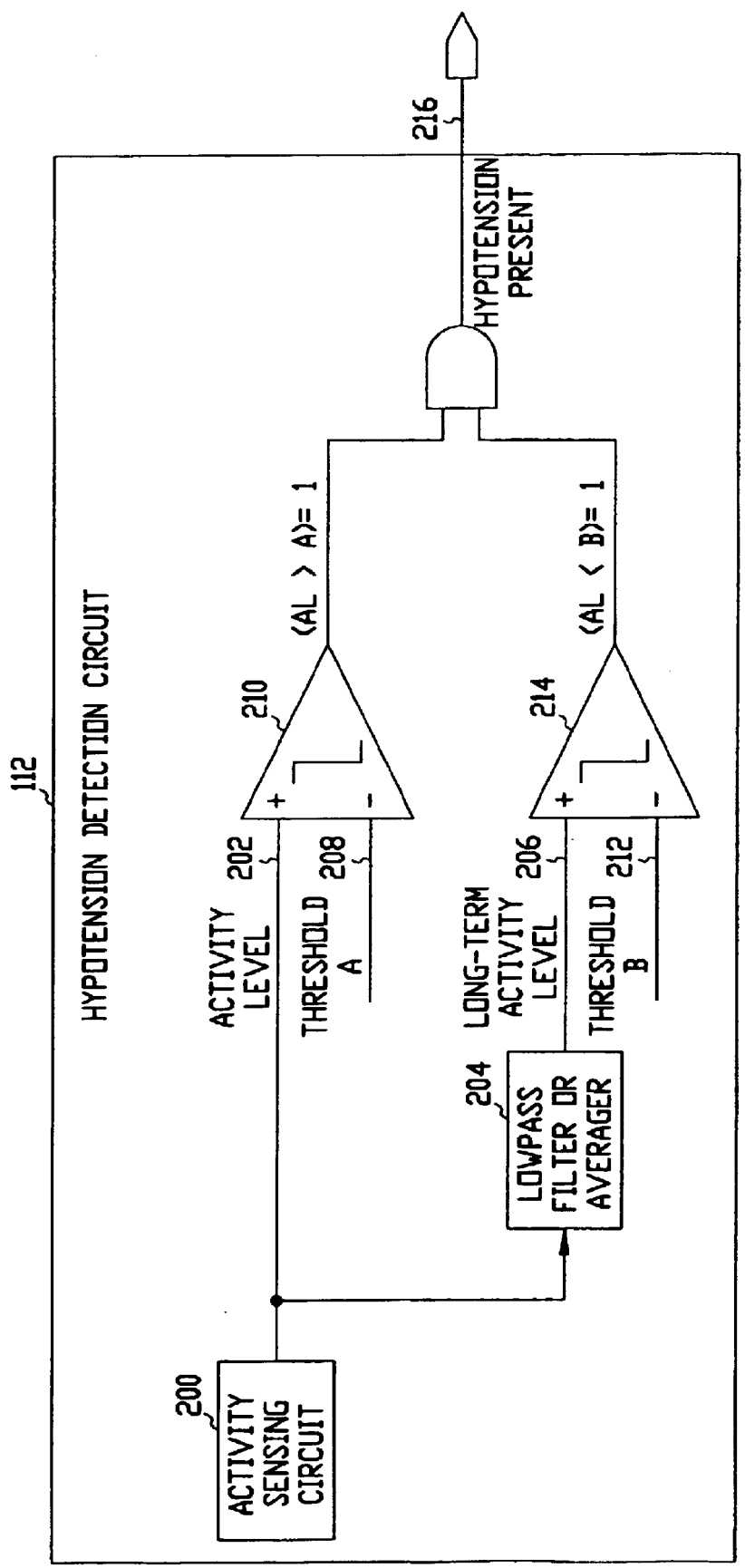
FIG. 2 is a block diagram example of a hypotension detection circuit using an activity sensing circuit.

FIG. 2 is a block diagram example of another hypotension detection circuit 112 using an activity sensing circuit 200. In one example, activity sensing circuit 200 includes an accelerometer circuit sensing the subject's motion, which is deemed correlative to the subject's activity, and providing at node 202 a resulting substantially instantaneous activity level (AL) output signal indicative of the subject's activity. In another example, activity sensing circuit 200 includes a respiration circuit (using the thoracic impedance technique discussed above or any other suitable technique for detecting a breathing rate) sensing the subject's breathing rate, which is deemed correlative to the subject's activity, and providing at node 202 a resulting substantially instantaneous AL output signal indicative of the subject's activity. An input of lowpass filter (or averager) 204 is coupled to receive the substantially instantaneous AL signal for lowpass filtering or averaging over an extended period of time, such as approximately between 15 minutes and 24 hours. Filter 204 outputs at node 206 a resulting long-term AL signal. The substantially instantaneous AL at node 202 is compared to a threshold value A at node 208 by comparator 210. The long-term AL at node 206 is compared to a threshold value B at node 212 by comparator 214. If the substantially instantaneous AL exceeds threshold A and the threshold B exceeds the long-term AL, then the subject is deemed to have transitioned from a period of rest to a period of activity. This detected transition is, in turn, deemed to correspond to an onset of orthostatic hypotension as communicated by the output of hypotension detection circuit, at node 216, to controller 110. The signal processing illustrated in FIG. 2 can be performed in either analog or digital domains.

Although hypotension detection circuit 112 and metabolic need sensor 116 are illustrated in FIG. 1 as being implemented separately, in certain examples these blocks may share certain components. For example, where an accelerometer is used as metabolic need sensor 116 and hypotension detection circuit 112 also uses an accelerometer-based activity sensing circuit 200, the same accelerometer can be used for both. Similarly, where thoracic impedance sensing of breathing is used as metabolic need sensor 116 and hypotension detection circuit 112 uses a thoracic impedance baseline for determining whether hypotension is present, the same test signal generation, receiving, and demodulation circuit could be used in both blocks, with appropriate separate processing of different frequency components of the thoracic impedance signal.

Figure 3:
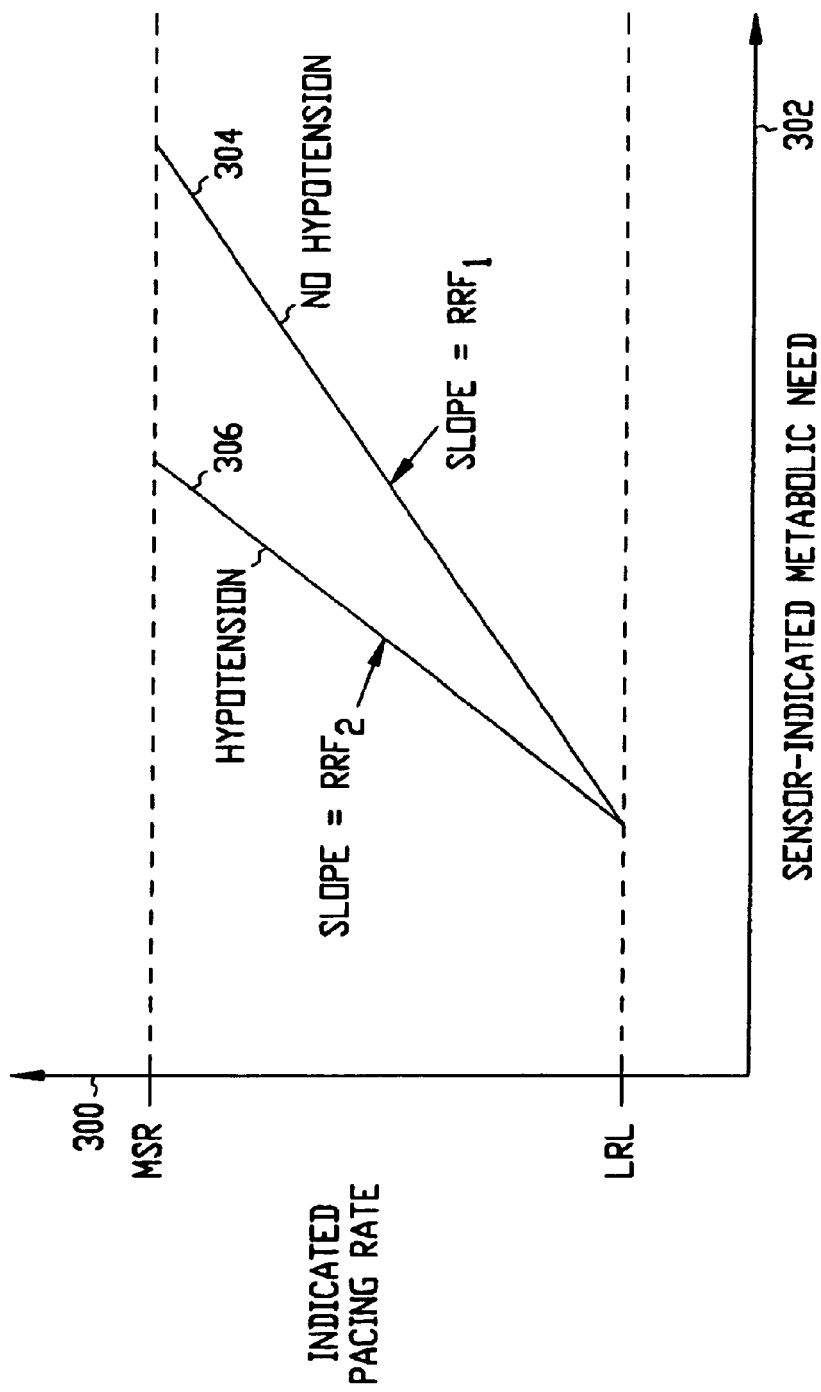
FIG. 3 is a graph example of one technique for determining the indicated pacing rate from the sensor-indicated metabolic need.

FIG. 3 is a graph example of one technique executed by controller 110 for determining the indicated pacing rate 300 from the sensor-indicated metabolic need 302 received by controller 110 from metabolic need sensor 116. In this example, line 304 indicates one mapping of metabolic need to the indicated pacing rate, which is bounded by a lower rate limit (LRL) and a maximum sensor rate (MSR). A greater metabolic need corresponds to a higher indicated pacing rate, therefore line 304 has a positive slope. The slope of line 304 is referred to as the rate response factor (RRF). The RRF is typically programmable to a particular value within a range of values. In operation, upon receiving an indication of a detected episode of hypotension from hypotension detection circuit 112, controller 110 increases the RRF from its programmed value, $RRF_1$, to a higher value, $RRF_2$, for a time period following the detection of hypotension, and then returns to $RRF_1$. In one example, this time period is approximately between 30 seconds and 10 minutes, such as about 2 minutes. During this time period, line 306 illustrates the mapping of metabolic need to indicated pacing rate. Thus, when hypotension is detected, a particular level of sensor-indicated metabolic need results in a higher value of the indicated pacing rate than when no hypotension is present. Controller 110 provides the indicated pacing rate to pacing therapy output circuit 114, which, in turn, provides pacing stimuli to heart 106 at the indicated pacing rate.

For example, when activity is used to indicate metabolic need, when hypotension is detected the indicated pacing rate is increased. The increase in indicated pacing rate is larger at higher activity levels than at lower activity levels. By increasing the indicated pacing rate in this manner, controller 110 effects a faster return of blood from the extremities to the thorax and head, thereby reducing or avoiding the symptoms of dizziness or fainting.

In an alternative example, rather than abruptly being stepped back from $RRF_2$ to $RRF_1$ following the time period initiated by the detected hypotension, the mapping slope more slowly decays, or otherwise incrementally steps back to the programmed value. In one example, the RRF approximately exponentially decays from $RRF_2$ to $RRF_1$, such as with a time constant that is approximately between 15 seconds and 10 minutes, such as about 1 minute. In another example, the RRF incrementally steps from $RRF_2$ to $RRF_1$ through a number of intermediate values that are substantially equally spaced between $RRF_2$ and $RRF_1$.

It is to be understood that the above description is intended to be illustrative, and not restrictive. For example, the above-discussed embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method including:
   detecting a thoracic impedance signal associated with a portion of a subject's thorax; and
   providing a therapy to the subject's heart at least in part in response to a baseline portion of the detected thoracic impedance below about 0.5 Hz indicating a fluid shift away from the thorax, the therapy assisting to shift fluid back toward the thorax, the providing the therapy including adjusting a rate response factor defining a relationship between (a) a pacing rate at which stimulations are delivered to the subject's heart; and (b) an activity level or respiration sensor signal that is correlative to the subject's metabolic need for cardiac output.

2. The method of claim 1, further including attenuating a high frequency component of the thoracic impedance signal.

3. A method including:
   detecting a thoracic impedance signal associated with a portion of a subject's thorax; and
   providing a therapy to the subject's heart at least in part in response to the detected thoracic impedance, including increasing a rate of pacing stimuli at least in part in response to an increase in the baseline portion of the thoracic impedance below about 0.5 Hz indicating a fluid shift away from the thorax, the therapy assisting to shift fluid back toward the thorax, the providing the therapy including adjusting a rate response factor defining a relationship between (a) a pacing rate at which stimulations are delivered to the subject's heart; and (b) an activity level or respiration sensor signal that is correlative to the subject's metabolic need for cardiac output.

4. The method of claim 3, further including detecting a motion of the subject and providing the therapy to the subject's heart based at least in part on the detected motion of the subject.

5. The method of claim 3, further including detecting a breathing of the subject and providing the therapy to the subject's heart based at least in part on the detected breathing.

6. The method of claim 5, in which providing the therapy to the subject's heart includes adjusting a rate of delivery of pacing stimuli based on frequency components of the thoracic impedance associated with fluid shift away from the thorax and associated with the subject's breathing.

7. The method of claim 3, in which the adjusting the rate response factor includes increasing the rate response factor, in response to the detecting the condition correlative to hypotension, such that a particular sensor indication of metabolic need results in a higher pacing rate after the increasing the rate response factor as compared to before the increasing the rate response factor.

8. The method of claim 3, further including attenuating a high frequency component of the thoracic impedance signal.

9. The method of claim 3, further including detecting a motion of the subject and providing the therapy to the subject's heart based at least in part on the detected motion of the subject.

10. The method of claim 3, further including detecting a breathing of the subject and providing the therapy to the subject's heart based at least in part on the detected breathing.

11. The method of claim 10, in which providing the therapy to the subject's heart includes adjusting a rate of delivery of pacing stimuli based on frequency components of the thoracic impedance associated with fluid shift away from the thorax and associated with the subject's breathing.

12. The method of claim 3, in which providing the therapy to the subject's heart includes increasing the rate response factor, in response to the detecting the condition correlative to hypotension, such that a particular sensor indication of metabolic need results in a higher pacing rate after the increasing the rate response factor as compared to before the increasing the rate response factor.

13. A method including:
    detecting a change in a thoracic impedance signal associated with a subject's thorax and including a thoracic fluid shift signal having a frequency component that is less than or equal to a cutoff frequency value that is between 0.01 Hz and 0.5 Hz inclusive; and
    increasing a rate of delivery of pacing stimuli at least in part in response to a detected increase in a baseline portion of the thoracic impedance signal indicating a fluid shift away from the thorax, the therapy assisting to shift fluid back toward the thorax and thereby decreasing the baseline portion of the thoracic impedance signal, the increasing the rate of delivery of pacing stimuli, the providing the therapy including adjusting a rate response factor defining a relationship between (a) a pacing rate at which stimulations are delivered to the subject's heart; and (b) an activity level or respiration sensor signal that is correlative to the subject's metabolic need for cardiac output.

14. The method of claim 13, which the cutoff frequency value is approximately 0.1 Hz.

15. The method of claim 13, further including detecting a motion of the subject and in which increasing the rate of delivery of pacing stimuli includes also basing the increase on the detected motion of the subject.

16. The method of claim 13, in which increasing the rate of delivery of pacing stimuli includes also basing the increase on a frequency component of the thoracic impedance associated with the subject's breathing.

17. A method including:
 detecting, using an implantable medical device to indicate thoracic hypotension resulting from a fluid shift away from the thorax using transthoracic impedance below about 0.5 Hz to indicate how much fluid is present in a thorax, both a hypotension associated with a change in a subject's posture and a hypotension that is not associated with a change in the subject's posture; and
 providing a therapy to the subject's heart at least in part in response to the detected hypotension, the therapy assisting to shift fluid back toward the thorax to reduce the hypotension, the providing the therapy including adjusting a rate response factor defining a relationship between (a) a pacing rate at which stimulations are delivered to the subject's heart; and (b) an activity level or respiration sensor signal that is correlative to the subject's metabolic need for cardiac output.

18. The method of claim 17, in which providing the therapy includes increasing a heart rate in response to the detected hypotension.

19. A cardiac rhythm management system, including:
 first and second electrodes configured for association with a portion of a subject's thorax;
 a thoracic signal detection module, coupled to the first and second electrodes for receiving a thoracic impedance signal and including an averager/lowpass filter that obtains a baseline portion of the thoracic impedance signal below about 0.5 Hz that is associated with a fluid shift away from the thorax; and
 means for performing a function of providing therapy to the subject's heart based on the baseline portion of the thoracic impedance signal, the therapy assisting to shift fluid back toward the thorax, the providing the therapy including adjusting a rate response factor defining a relationship between (a) a pacing rate at which stimulations are delivered to the subject's heart; and (b) an activity level or respiration sensor signal that is correlative to the subject's metabolic need for cardiac output.

20. A cardiac rhythm management system, including:
 first and second electrodes configured for association with a portion of a subject's thorax;
 a thoracic signal detection module, coupled to the first and second electrodes for receiving a thoracic impedance signal and including an averager/lowpass filter that obtains a baseline portion of the thoracic impedance signal below about 0.5 Hz that is associated with a fluid shift away from the thorax; and
 a pacing therapy output circuit providing therapy to the subject's heart in response to the baseline portion of the thoracic impedance signal indicating a fluid shift away from the thorax, the therapy assisting to shift fluid back toward the thorax, the therapy including adjusting a rate response factor defining a relationship between (a) a pacing rate at which stimulations are delivered to the subject's heart; and (b) an activity level or respiration sensor signal that is correlative to the subject's metabolic need for cardiac output.

21. A cardiac rhythm management system, including:
 first and second electrodes configured for association with a portion of a subject's thorax;
 means, coupled to the first and second electrodes for receiving a thoracic impedance signal, for performing the function of obtaining a baseline portion of the thoracic impedance signal below about 0.5 Hz that is associated with a fluid shift away from the thorax; and
 a pacing therapy output circuit providing therapy to the subject's heart in response to the baseline portion of the thoracic impedance signal indicating a fluid shift away from the thorax, the therapy assisting to shift fluid back toward the thorax, therapy including adjusting a rate response factor defining a relationship between (a) a pacing rate at which stimulations are delivered to the subject's heart; and (b) an activity level or respiration sensor signal that is correlative to the subject's metabolic need for cardiac output.

22. A cardiac rhythm management system, including:
 first and second electrodes configured for association with a portion of a subject's thorax;
 a thoracic signal detection module, coupled to the first and second electrodes;
 third and fourth electrodes configured for association with a portion of a subject's heart;
 a pacing therapy output module, coupled to the third and fourth electrodes; and
 a pacing stimuli rate controller, coupled to the thoracic signal detection module for receiving a thoracic impedance signal including a baseline signal component associated with a fluid shift away from the thorax, the controller also coupled to the pacing therapy output module for adjusting the rate of delivery of pacing stimuli at least in part in response to the portion of the thoracic impedance signal below about 0.5 Hz associated with the thoracic fluid shift away from the thorax, the adjusting the rate of delivery of pacing stimuli assisting to shift fluid back toward the thorax, the providing the therapy including adjusting a rate response factor defining a relationship between (a) a pacing rate at which stimulations are delivered to the subject's heart; and (b) an activity level or respiration sensor signal that is correlative to the subject's metabolic need for cardiac output.

23. The system of claim 22, in which at least one of the third and fourth electrodes is the same electrode as one of the first and second electrodes.

24. The system of claim 22, further including a thoracic test signal generator configured for association with the thorax for providing energy to the thorax for detecting thoracic impedance.

25. The system of claim 22, in which the rate controller further includes a lowpass filter coupled to the thoracic signal detection module.

26. The system of claim 25, in which the lowpass filter obtains the baseline portion of the thoracic impedance signal that is associated with a fluid shift away from the heart.

27. The system of claim 26, in which the lowpass filter attenuates a breathing portion of the thoracic impedance signal.

28. The system of claim 26, in which the lowpass filter attenuates a cardiac stroke portion of the thoracic impedance signal.

29. The system of claim 25, in which the lowpass filter attenuates a component of the thoracic impedance not associated with the thoracic fluid shift.

30. The system of claim 25, in which the lowpass filter includes an effective cutoff frequency that is between 0.01 Hz and 0.5 Hz.

31. The system of claim 30, in which the lowpass filter includes a cutoff frequency that is approximately equal to 0.1 Hz.

32. The system of claim 22, in which the controller includes a blending module for adjusting the rate of delivering pacing stimuli based on thoracic fluid shift and at least one of:

(a) a breathing by the subject; and (b) a motion of the subject.

33. A cardiac rhythm management system, including:

first and second electrodes configured for association with a portion of a subject's thorax;

a thoracic signal detection module, coupled to the first and second electrodes;

thoracic test signal generator configured for association with the thorax for providing energy to the thorax for detecting thoracic impedance;

third and fourth electrodes configured for association with a portion of a subject's heart;

a pacing therapy output module, coupled to the third and fourth electrodes; and a pacing stimuli rate control module, coupled to the thoracic signal detection module for receiving a thoracic impedance signal, the rate control module including a lowpass filter for distinguishing a baseline thoracic fluid shift signal below about 0.5 Hz from another variation in thoracic impedance, the rate control module also coupled to the pacing therapy output module for adjusting the rate of delivery of pacing stimuli at least in part in response to the thoracic fluid shift signal indicating a fluid shift away from the thorax, the adjusting the rate of delivery of pacing stimuli assisting to shift fluid back toward the thorax, the adjusting the rate of delivery including adjusting a rate response factor defining a relationship between (a) a pacing rate at which stimulations are delivered to the subject's heart; and (b) an activity level or respiration sensor signal that is correlative to the subject's metabolic need for cardiac output.

34. A cardiac rhythm management system, including:

means for detecting a thoracic impedance;

first and second electrodes, configured for association with a portion of a subject's heart;

a pacing therapy output module, coupled to the first and second electrodes; and a pacing stimuli rate control module, coupled to the means for detecting thoracic impedance and the pacing therapy output module, the rate control module adjusting a rate of delivery of pacing stimuli at least in part in response to a baseline portion of the thoracic impedance below about 0.5 Hz indicating a thoracic fluid shift away from the thorax, the adjusting the rate of delivery of pacing stimuli assisting to shift fluid back toward the thorax, the adjusting the rate of delivery including adjusting a rate response factor defining a relationship between (a) a pacing rate at which stimulations are delivered to the subject's heart; and (b) an activity level or respiration sensor signal that is correlative to the subject's metabolic need for cardiac output.

* * * * *

UNITED STATES PATENT AND TRADEMARK OFFICE
CERTIFICATE OF CORRECTION

PATENT NO. : 6,907,288 B2
APPLICATION NO. : 09/879665
DATED : June 14, 2005
INVENTOR(S) : Daum Page 1 of 1

It is certified that error appears in the above-identified patent and that said Letters Patent is hereby corrected as shown below:

In column 9, line 1, in Claim 14, after "13," insert - - in - -.

Signed and Sealed this

First Day of August, 2006

JON W. DUDAS
*Director of the United States Patent and Trademark Office*